US009919045B1

(12) United States Patent
Boukhvalova et al.

(10) Patent No.: US 9,919,045 B1
(45) Date of Patent: Mar. 20, 2018

(54) HERPES SIMPLEX VIRUS VACCINE COMPOSITIONS AND METHODS OF PRODUCTION AND USE THEREOF

(71) Applicant: Sigmovir Biosystems, Inc., Rockville, MD (US)

(72) Inventors: Marina S. Boukhvalova, Potomac, MD (US); Jorge C. G. Blanco, Washington, DC (US)

(73) Assignee: Sigmovir Biosystems, Inc., Rockville, MD (US)

( * ) Notice: Subject to any disclaimer, the term of this patent is extended or adjusted under 35 U.S.C. 154(b) by 25 days.

(21) Appl. No.: 15/218,057

(22) Filed: Jul. 24, 2016

Related U.S. Application Data

(60) Provisional application No. 62/196,564, filed on Jul. 24, 2015.

(51) Int. Cl.
*A61K 39/245* (2006.01)
*C12N 7/00* (2006.01)
*C07K 14/005* (2006.01)
*A61K 39/00* (2006.01)

(52) U.S. Cl.
CPC .......... *A61K 39/245* (2013.01); *C07K 14/005* (2013.01); *C12N 7/00* (2013.01); *A61K 2039/515* (2013.01); *A61K 2039/55505* (2013.01); *A61K 2039/55511* (2013.01); *A61K 2039/55572* (2013.01); *A61K 2039/55588* (2013.01); *C12N 2710/16621* (2013.01); *C12N 2710/16634* (2013.01); *C12N 2710/16651* (2013.01); *C12N 2710/16671* (2013.01)

(58) Field of Classification Search
CPC ............ C12N 7/00; C12N 2760/16151; C12N 2760/20252; C12N 15/86; C12N 2760/20251; C12N 2510/02; C12N 2700/00; C12N 2710/10343; C12N 2720/12351; C12N 7/02; A61K 2039/525; A61K 2039/5254; A61K 2039/5252; C07K 14/005
See application file for complete search history.

(56) References Cited

U.S. PATENT DOCUMENTS

2012/0107349 A1* 5/2012 Baker, Jr. ............. A61K 9/1075 424/203.1
2015/0050318 A1* 2/2015 Baker, Jr. ............. A61K 9/1075 424/203.1

FOREIGN PATENT DOCUMENTS

CA 2090303 A1 * 9/1993 ........... A61K 39/245
WO WO 2016087479 A1 * 6/2016 ............. A61K 47/26

OTHER PUBLICATIONS

Marshak JO, Dong L, Koelle DM. The murine intravaginal HSV-2 challenge model for investigation of DNA vaccines. Methods Mol Biol. 2014;1144:305-27.*
Koelle DM, Corey L. Recent progress in herpes simplex virus immunobiology and vaccine research. Clin Microbiol Rev. Jan. 2003;16(1):96-113.*
Jennings R, Erturk M. Comparative studies of HSV-1 antigens solubilised from infected cells by using non-ionic or zwitterionic detergents. J Med Virol. Jun. 1990;31(2):98-108.*
Mukhlis FA, Jennings R, Stephenson TJ, Quasim T, Potter CW. Characterization and immunogenicity of HSV-1 antigens obtained following zwitterionic detergent treatment. Vaccine. Sep. 1986;4(3):191-6.*
Bernstein DI, Cardin RD, Bravo FJ, Strasser JE, Farley N, Chalk C, Lay M, Fairman J. Potent adjuvant activity of cationic liposome-DNA complexes for genital herpes vaccines. Clin Vaccine Immunol. May 2009;16(5):699-705. Epub Mar. 11, 2009.*
Kino Y, Eto T, Nishiyama K, Ohtomo N, Mori R. Immunogenicity of purified glycoprotein gB of herpes simplex virus. Arch Virol. 1986;89(1-4):69-80.*
Belshe, R.B. et al., Efficacy Results of a Trial of a Herpes Simplex Vaccine, New England Journal of Medicine, Jan. 2012, 366(1):34-43.
Bernstein, D.I. et al., Epidemiology, Clinical Presentation, and Antibody Response to Primary Infection with Herpes Simplex Virus Type 1 and Type 2 in Young Women, Clinical Infectious Disease, Feb. 2013, 56:344-351.
Blanco, J.C.G. et al., Receptor Characterization and Susceptibility of Cotton Rats to Avian and 2009 Pandemic Influenza Virus Strains, Journal of Virology, Feb. 2013, 87(4):2036-2045.
Blanco, J.C.G. et al., Prophylactic Antibody Treatment and Intramuscular Immunization Reduce Infectious Human Rhinovirus 16 Load in the Lower Respiratory Tract of Challenged Cotton Rats, Trials Vaccinology, 2014, 3:52-60.
Boukhvalova, M.S. et al., The Cotton Rat Model of Respiratory Viral Infections Pathogenesis and Immunity, Biologicals, Jun. 2009, 37(3):152-159.
Boukhvalova, M.S. et al., Efficacy of the Herpes Simplex Virus 2 (HSV-2) Glycoprotein D/AS04 Vaccine against Genital HSV-2 and HSV-1 Infection and Disease in the Cotton Rat Sigmodon hispidus Model, Journal of Virology, Oct. 2015, 89(19):9825-9840.
Bourne, N. et al., Impact of Immunization with Glycoprotein D2/AS04 on Herpes Simplex Virus Type 2 Shedding into the Genital Tract in Guinea Pigs That Become Infected, The Journal of Infectious Diseases, Dec. 2005, 192:2117-2123.
Bourne, N. et al., Herpes Simplex Virus (HSV) Type 2 Glycoprotein D Subunit Vaccines and Protection against Genital HSV-1 or HSV-2 Disease in Guinea Pigs, The Journal of Infectious Diseases, Feb. 2003, 187:542-549.
Bradley, H. et al., Seroprevalence of Herpes Simplex Virus Types 1 and 2—United States, 1999-2010, The Journal of Infectious Diseases, Feb. 2014, 209:325-333.
Cowan, F. et al., HIV in adolescents in sub-Saharan Africa, Current Opinion in HIV and AIDS, 2009, 4:288-293.

(Continued)

*Primary Examiner* — Rachel B Gill
(74) *Attorney, Agent, or Firm* — George W. Cox

(57) ABSTRACT

Vaccine compositions are disclosed for vaccinating a human or animal against herpes simplex virus infections. Also provided are methods of producing vaccines against herpes simplex virus and methods of using such vaccines to prevent or ameliorate herpes simplex virus-associated disease such as genital herpes.

20 Claims, 17 Drawing Sheets

(56) References Cited

OTHER PUBLICATIONS

Freeman, E.E. et al., Herpes simplex virus 2 infection increases HIV acquisition in men and women: systematic review and meta-analysis of longitudinal studies, AIDS, 2006, 20:73-83.
Hoshino, Y. et al., Comparative Efficacy and Immunogenicity of Replication-Defective, Recombinant Glycoprotein, and DNA Vaccines for Herpes Simplex Virus 2 Infections in Mice and Guinea Pigs, Journal of Virology, Jan. 2005, 79:410-418.
Niewiesk, S. et al., Diversifying animal models: the use of hispid cotton rats (Sigmodon hispidus) in infectious diseases, Laboratory Animals, 2002, 36:357-372.
Pereira, V.S.S. et al., Herpes simplex virus type 1 is the main cause of genital herpes in women of Natal, Brazil, European Journal of Obstetrics & Gynecology and Reproductive Biology, 2012, 161:190-193.
Saba, E. et al., HIV-1 sexual transmission: early events of HIV-1 infection of human cervico-vaginal tissue in an optimized ex vivo model, Mucosal Immunology, May 2010, 3(3):280-290.
Stanberry, L.R. et al., Gylcoprotein-D-Adjuvant Vaccine to Prevent Genital Herpes, The New England Journal of Medicine, Nov. 2002, 347(21):1652-1661.
Xu, F. et al., Seroprevalence of Herpes Simplex Virus Type 2 Among Persons Aged 14-49 Years—United States, 2005-2008, Morbidity and Mortality Weekly Report, CDC, Apr. 2010, 59(15), 456-459.
Xu, F. et al., Trends in Herpes Simplex Virus Type 1 and Type 2 Seroprevalence in the United States, Journal of the American Medical Association, Aug. 2006, 296(8):964-973.
Laing, K. J. et al., Immunology in the Clinic Review Series; focus on host responses: T cell responses to herpes simplex viruses, Clinical & Experimental Immunology, 2011, 167:47-58.
Ryder, N. et al., Increasing role of herpes simplex virus type 1 in first-episode anogenital herpes in heterosexual women and younger men who have sex with men,1992-2006, Sexually Transmitted Infection, 2009, 85:416-419.

* cited by examiner

Fig. 1A

| Immuniz. | Infection | animal # | Day post-infection | | | | | | | | | | Disease |
|---|---|---|---|---|---|---|---|---|---|---|---|---|---|
| | | | d0 | d4 | d7 | d9 | d11 | d14 | d16 | d18 | d21 | d28 | |
| PBS | Uninfect. | 90633 | 0 | 0 | 0 | 0 | 0 | 0 | 0 | 0 | 0 | 0 | 0/3 |
| | | 90634 | 0 | 0 | 0 | 0 | 0 | 0 | 0 | 0 | 0 | 0 | |
| | | 90635 | 0 | 0 | 0 | 0 | 0 | 0 | 0 | 0 | 0 | 0 | |
| PBS | Infected with HSV-2 5×10^4 PFU per animal | 90636 | 0 | 1 | 1 | | | | | | | | 5/5 |
| | | 90637 | 0 | 1 | | | | | | | | | |
| | | 90638 | 0 | 1 | 1 | | | | | | | | |
| | | 90639 | 0 | 1 | | | | | | | | | |
| | | 90640 | 0 | 1 | | | | | | | | | |
| gD 2 µg | | 90641 | 0 | 0 | 0 | 0 | 0 | 0 | 0 | 0 | | | 3/5 |
| | | 90642 | 0 | 0 | 0 | 0 | 0 | 0 | 0 | 0 | 0 | 0 | |
| | | 90643 | 0 | 1 | 1 | | | | | | | | |
| | | 90644 | 0 | 0 | 0 | 0 | 1 | 1 | 1 | 1 | 0 | 0 | |
| | | 90645 | 0 | 0 | 0 | 0 | 0 | 0 | 0 | 0 | 0 | 0 | |
| gD 0.3 µg | | 90646 | 0 | 0 | 1 | 1 | 1 | 1 | 1 | | | | 5/5 |
| | | 90647 | 0 | 1 | 1 | | | | | | | | |
| | | 90648 | 0 | 1 | | | | | | | | | |
| | | 90649 | 0 | 1 | | | | | | | | | |
| | | 90650 | 0 | 1 | 1 | | | | | | | | |
| gD 0.06 µg | | 90651 | 0 | 0 | 0 | 1 | 1 | 1 | 1 | 1 | 0 | 0 | 5/5 |
| | | 90652 | 0 | | | | | | | | | | |
| | | 90653 | 0 | | | | | | | | | | |
| | | 90654 | 0 | | | | | | | | | | |
| | | 90655 | 0 | | | | | | | | | | |
| Fendrix | | 90656 | 0 | | | | | | | | | | 5/5 |
| | | 90657 | 0 | 1 | 1 | 1 | | | | | | | |
| | | 90658 | 0 | 1 | | | | | | | | | |
| | | 90659 | 0 | 1 | 1 | 1 | | | | | | | |
| | | 90660 | 0 | 1 | | | | | | | | | |
| UV-HSV | | 90661 | 0 | 0 | 0 | 0 | 0 | 0 | 0 | 0 | 0 | 0 | 0/4 |
| | | 90662 | 0 | 0 | 0 | 0 | 0 | 0 | 0 | 0 | 0 | 0 | |
| | | 90663 | 0 | 0 | 0 | 0 | 0 | 0 | 0 | 0 | 0 | 0 | |
| | | 90664 | 0 | 0 | 0 | 0 | 0 | 0 | 0 | 0 | 0 | 0 | |

*p<0.05 comp to Fendrix

*p<0.05 comp to Fendrix

Fig. 3A

| Immuniz. | Infection | animal # | Day post-infection | | | | | | | | | | Disease |
|---|---|---|---|---|---|---|---|---|---|---|---|---|---|
| | | | d2 | d4 | d7 | d11 | d14 | d16 | d18 | d21 | d23 | d28 | |
| Fendrix | Infected with HSV-1 2*10⁶ PFU per animal | 98132 | 0 | 1 | 1 | 1 | 1 | 1 | 1 | 1 | | | 8/8 |
| | | 98133 | 0 | 1 | | | | | | | | | |
| | | 98134 | 0 | 1 | 1 | 1 | 1 | 1 | | | | | |
| | | 98135 | 0 | 1 | 1 | 1 | 1 | 1 | | | | | |
| | | 98136 | 0 | 1 | | | | | | | | | |
| | | 98137 | 0 | 0 | 1 | 1 | 1 | 1 | 1 | 1 | 1 | 1 | |
| | | 98138 | 0 | 0 | 1 | 1 | 1 | 1 | 1 | | | | |
| | | 98139 | 0 | 0 | 1 | 1 | 1 | 1 | | | | | |
| gD 2 mg | | 98140 | 0 | 0 | 0 | 0 | 0 | 0 | 0 | 0 | 0 | 0 | 0/8* |
| | | 98141 | 0 | 0 | 0 | 0 | 0 | 0 | 0 | 0 | 0 | 0 | |
| | | 98142 | 0 | 0 | 0 | 0 | 0 | 0 | 0 | 0 | 0 | 0 | |
| | | 98143 | 0 | 0 | 0 | 0 | 0 | 0 | 0 | 0 | 0 | 0 | |
| | | 98144 | 0 | 0 | 0 | 0 | 0 | 0 | 0 | 0 | 0 | 0 | |
| | | 98145 | 0 | 0 | 0 | 0 | 0 | 0 | 0 | 0 | 0 | 0 | |
| | | 98146 | 0 | 0 | 0 | 0 | 0 | 0 | 0 | 0 | 0 | 0 | |
| | | 98147 | 0 | 0 | 0 | 0 | 0 | 0 | 0 | 0 | 0 | 0 | |
| gD 0.3 mg | | 98148 | 0 | 0 | 0 | 0 | 0 | 0 | 1 | 1 | 0 | 0 | 6/8* |
| | | 98149 | 0 | 0 | 0 | 0 | 0 | 0 | 1 | 1 | 1 | 1 | |
| | | 98150 | 0 | 0 | 0 | 0 | 0 | 0 | 0 | 0 | 0 | 0 | |
| | | 98151 | 0 | 0 | 0 | 0 | 0 | 0 | 0 | 0 | | | |
| | | 98152 | 0 | 0 | 0 | 0 | 0 | 0 | 1 | 1 | 1 | 1 | |
| | | 98153 | 0 | 0 | 0 | 0 | 0 | 0 | 1 | 1 | | | |
| | | 98154 | 0 | 0 | 0 | 0 | 0 | 0 | 0 | 0 | 0 | 0 | |
| | | 98155 | 0 | 0 | 0 | 0 | 0 | 0 | 1 | 1 | 1 | 1 | |
| gD 0.06 mg | | 98156 | 0 | 0 | 0 | 0 | 1 | 1 | 1 | 1 | 1 | 0 | 5/8 |
| | | 98157 | 0 | 0 | 0 | 0 | 1 | 1 | 1 | 1 | | | |
| | | 98158 | 0 | 0 | 0 | 0 | 1 | 1 | 1 | 1 | 1 | 0 | |
| | | 98159 | 0 | 1 | | | | | | | | | |
| | | 98160 | 0 | 0 | 0 | 0 | 1 | 1 | 1 | 1 | 1 | 0 | |
| | | 98161 | 0 | 0 | 0 | 0 | 0 | 0 | 0 | 0 | 0 | 0 | |
| | | 98162 | 0 | 0 | 0 | 0 | 0 | 0 | 0 | 0 | 0 | 0 | |
| | | 98163 | 0 | 0 | 0 | 0 | 0 | 0 | 0 | 0 | 0 | 0 | |
| UV-HSV | | 99496 | 0 | 0 | 0 | 0 | 0 | 0 | 0 | 0 | 0 | 0 | 1/5* |
| | | 99497 | 0 | 0 | 0 | 0 | 0 | 0 | 0 | 0 | 0 | 0 | |
| | | 99498 | 0 | 0 | 0 | 0 | 0 | 0 | 0 | 0 | 0 | 0 | |
| | | 99499 | 0 | 0 | 0 | 0 | 0 | 0 | 0 | 0 | | | |
| | | 99500 | 0 | 0 | 0 | 0 | 0 | 0 | 0 | 0 | 0 | 0 | |

*p<0.05 comp to Fendrix

*p<0.05 comp to Fendrix

Fig. 4A

| Antigen | Adjuvant | Animal # | d1 | d4 | d5 | d6 | d9 | d10 | d15 | d23 | d30 |
|---|---|---|---|---|---|---|---|---|---|---|---|
| Vero/HSV | MPL+ TDM | 108391 | 0 | 0 | 0 | 0 | 0 | 0 | 0 | 0 | 0 |
| | | 108392 | 0 | 0 | 0 | 0 | 0 | 0 | 0 | 0 | 0 |
| | | 108393 | 0 | 0 | 0 | 0 | 0 | 0 | 0 | 0 | 0 |
| | | 108394 | 0 | 0 | 0 | 0 | 0 | 0 | 0 | 0 | 0 |
| | | 108395 | 0 | 0 | 0 | 0 | 0 | 0 | 0 | 0 | 0 |
| | MPL+ TDM+ CWS | 101856 | 0 | 0 | 0 | 0 | 0 | 0 | 0 | 0 | 0 |
| | | 101857 | 0 | 0 | 0 | 0 | 0 | 0 | 0 | 0 | 0 |
| | | 101858 | 0 | 0 | 0 | 0 | 0 | 0 | 0 | 0 | 0 |
| | | 101859 | 0 | 0 | 0 | 0 | 0 | 0 | 0 | 0 | 0 |
| | | 101860 | 0 | 0 | 0 | 0 | 0 | 0 | 0 | 0 | 0 |
| | MPL+ Alum | 108806 | 0 | 0 | 0 | 0 | 0 | 0 | 0 | 0 | 0 |
| | | 108807 | 0 | 0 | 0 | 0 | 0 | 0 | 0 | 0 | 0 |
| | | 108808 | 0 | 0 | 0 | 0 | 0 | 0 | 0 | 0 | 0 |
| | | 108809 | 0 | 0 | 0 | 0 | 0 | 0 | 0 | 0 | 0 |
| | | 1088010 | 0 | 0 | 0 | 0 | 0 | 0 | 0 | 0 | 0 |
| | Alum | 108396 | 0 | 0 | 0 | 0 | 0 | 0 | 0 | 0 | 0 |
| | | 108397 | 0 | 0 | 0 | 0 | 0 | 0 | 0 | 0 | 0 |
| | | 108398 | 0 | 0 | 0 | 0 | 0 | 0 | 0 | 0 | 0 |
| | | 108399 | 0 | 0 | | | | | | | |
| | | 108400 | 0 | 0 | 0 | 0 | 0 | 0 | 0 | 0 | 0 |
| | | 108801 | 0 | 0 | 0 | 0 | | | | | |
| | | 108802 | 0 | 0 | 0 | 0 | 0 | 0 | 0 | 0 | 0 |
| | | 108803 | 0 | 0 | 0 | 0 | 0 | 0 | 0 | 0 | 0 |
| | - | 108411 | 0 | 0 | 0 | 0 | 0 | | | | |
| | | 108412 | 0 | 0 | 0 | 0 | 0 | 0 | 0 | 0 | |
| | | 108413 | 0 | 0 | 0 | 0 | 0 | | | | |
| | | 108414 | 0 | 0 | 0 | 0 | 0 | | | | |
| | | 108415 | 0 | 0 | 0 | 0 | 0 | 0 | 0 | 0 | 0 |
| PBS | - | 108416 | 0 | 0 | 0 | | | | | | |
| | | 108417 | 0 | 0 | 0 | 0 | 0 | | | | |
| | | 108418 | 0 | 0 | 0 | | | | | | |
| | | 108419 | 0 | 0 | | | | | | | |
| | | 108420 | 0 | 0 | 0 | | | | | | |

HERPES SIMPLEX VIRUS VACCINE COMPOSITIONS AND METHODS OF PRODUCTION AND USE THEREOF

CROSS-REFERENCE TO RELATED APPLICATION

This application claims the benefit of U.S. Provisional Patent Application Ser. No. 62/196,564, filed Jul. 24, 2015, which is hereby incorporated by reference in its entirety.

BACKGROUND OF THE INVENTION

The present invention relates generally to protection against herpes simplex virus (HSV) infection. While the invention is subject to a wide range of applications, it relates especially to a vaccine suited for vaccination of animals and humans against herpes simplex virus 2 (HSV-2) and herpes simplex virus 1 (HSV-1) and the prevention of associated illness such as genital herpes. In addition, the invention provides methods of preparing a vaccine against HSV-2 and HSV-1 infections and methods of use thereof.

The disease burden associated with HSV-2 infection, an important cause of genital herpes worldwide, is high and presents an additional threat due to its association with an increased risk of human immunodeficiency virus (HIV) acquisition and transmission (Xu F et al. 2006. *JAMA* 296(8), 964-973; Freeman E E et al. 2006. *AIDS* 20(1), 73-83; Cowan F & Pettifor A. 2009. *Curr Opin HIV AIDS* 4(4), 288-293). Globally, HSV-2 is a major health threat with 16% of the US population infected by age 30 and 50-90% of the population in sub-Saharan Africa (Cowan F & Pettifor A. 2009. *Curr Opin HIV AIDS* 4(4), 288-293; Xu F et al. 2010. *Morbidity and Mortality Weekly Report, CDC* 59(15), 456-459; Bradley H et al. 2014. *J Infect Dis* 209(3):325-33). Recent reports emphasize the importance of HSV-1 as an important etiologic agent of genital herpes particularly in the US and other developed countries (Ryder N et al. 2009. *Sex Transm Infect* 85(6):416-9; Pereira V S et al. 2012. *Eur J Obstet Gynecol Reprod Biol* 161(2):190-3; Bernstein D I et al. 2013. *Clin Infect Dis* 56(3):344-51). Seroprevalence of HSV-1 among 14-49-year-old in the US reached 53.9% in 2005-2010 (Bradley H et al. 2014. *J Infect Dis* 209(3):325-33). No effective vaccine is available to prevent the acquisition or spread of either HSV serotype.

Vaccine efforts focus on subunit vaccines that include viral envelope glycoproteins alone or in combination with other structural and non-structural viral proteins, replication-defective viruses, and vectored and peptide-based vaccines (Stanberry L R. 2004. *Herpes* 11 Suppl 3, 161A-169A; Koelle D M & Corey L. 2008. *Annu Rev Med* 59, 381-395; Halford W P. 2014. *Expert Rev Vaccines* 13(6):691-710). Subunit vaccines based on the HSV-2 glycoprotein D (gD-2) were advanced to clinical trials based on efficacy in small animal models (Bourne N et al. 2003. *J Infect Dis* 187(4), 542-549; Bourne N et al. 2005. *J Infect Dis* 192(12), 2117-2123; Hoshino Y et al. 2005. *J Virol* 79(1):410-8). However, the results of the most recent gD-2 subunit vaccine clinical trials were unexpected (Stanberry L R. 2004. *Herpes* 11 Suppl 3, 161A-169A; Belshe R B et al. 2012. *N Engl J Med* 366(1), 34-43). Two double-blind randomized Phase 2 studies of the gD-2 vaccine Simplirix™, containing aluminum salt and monophosphoryl lipid A (MPL) adjuvants (gD/AS04), found 73% and 74% efficacy against genital disease in HSV-discordant couples in women who were seronegative for both HSV-1 and HSV-2, but no protection in women who were seropositive for HSV-1 at enrollment or in men (Stanberry L R et al. 2002. *N Engl J Med* 347(21), 1652-1661). The subsequent Phase 3 trial, which was conducted among 8,323 women 18 to 30 years of age who were seronegative for both HSV-1 and HSV-2 at enrollment, revealed that gD/AS04 vaccine was not effective against HSV-2 genital herpes disease despite inducing HSV-specific enzyme-linked immunosorbent assay (ELISA) and neutralizing antibodies (Belshe R B et al. 2012. *N Engl J Med* 366(1), 34-43). However, the vaccine did provide 58% (95% CI 12 to 80) protection against HSV-1 genital disease (Belshe R B et al. 2012. *N Engl J Med* 366(1), 34-43). These findings highlight the need for new preclinical models that may prove more predictive of vaccine trial outcomes.

Genital herpes caused by HSV-1 or HSV-2 is a debilitating disease that also predisposes individuals to acquisition of HIV. In spite of the high health burden of genital herpes, there is still no effective vaccine or intervention against the disease. The significant gap in knowledge on genital herpes pathogenesis has been further highlighted by the recent failure of HSV-2 vaccine Simplirix™ (gD/AS04) to protect humans against HSV-2 and the surprising finding that the vaccine protected against HSV-1 genital herpes instead. The failure of HSV-2 vaccine Simplirix™ (gD/AS04) emphasizes the need for alternative vaccine strategies and the identification of new correlates of protection against genital herpes. Thus, there remains a need for safe and effective approaches to protect animals and humans against HSV-2 and HSV-1, and their associated diseases such as genital herpes. In particular, there remains a need for specific vaccines to prevent HSV-2 and HSV-1 infections, and for therapeutic approaches to prevent illnesses associated with HSV-2 and HSV-1 infections. The data obtained in previous studies suggested that efficient protection against genital herpes is associated with a polyvalent antibody response against antigens present in extracts of HSV-infected Vero cells (Boukhvalova et al. 2015. *J Virol* 89(19), 9825-40).

SUMMARY OF THE INVENTION

Accordingly, an object of the invention is to provide a vaccine composition that elicits a prophylactically effective (and/or a therapeutically effective) immune response in an animal or human against HSV. In one representative embodiment, the vaccine composition includes an extract of detergent-treated HSV-infected cells and an adjuvant. In one representative embodiment, HSV is HSV-2. In alternative embodiments, HSV may be, for example, HSV-1 alone or the combination of HSV-2 and HSV-1. In certain embodiments, the virus used to infect cells may include, for example, wild type virus, clinical isolate of virus, recombinant virus, live virus, and vectored-expression systems encoding viral proteins, which may be used individually or in combination. In a representative embodiment, the cells are Vero cells. In representative embodiments, the adjuvant may be, for example, alum alone, a combination of monophosphoryl lipid A (MPL) and alum, a combination of MPL and trehalose 6,6'-dimycolate (TDM), and a combination of MPL, TDM, and biologically-active components of cell wall skeleton.

Another object of the invention is to provide a method of preparing an HSV vaccine antigen. In one representative embodiment, the HSV vaccine antigen is prepared by propagating Vero cells, infecting the cells with HSV-2, HSV-1, or a combination of HSV-2 and HSV-1, lysing the infected cells to obtain a cell extract by treating the cells with a detergent and optionally subjecting the detergent-treated cells to at least one cycle of freezing and thawing, and purifying the cell extract such that the cell extract can be used as the HSV vaccine antigen in a vaccination or immunization of an animal or human. In certain aspects of a representative embodiment, the detergent may be IGEPAL. However, other detergents may be suitable as well. In certain aspects of a representative embodiment, the cell extract or lysate may be purified by removal of DNA, centrifugation, dialysis, and the like. The purified cell extract may be subjected to additional processing to precipitate proteins and obtain HSV-enriched proteins. HSV-enriched proteins may include, for example, high molecular weight proteins, low molecular weight proteins, glycosylated proteins, lipid-associated proteins, charged proteins, hydrophobic proteins, hydrophilic proteins, other post-translationally modified proteins, and combinations thereof. In a representative embodiment, the purified cell extract may be subjected to additional processing to reduce the presence of Vero cell native proteins.

Another object of the invention is to provide a method of vaccinating an animal or human against HSV and HSV-associated disease (including, for example, genital herpes). In one representative embodiment, a method is provided for administering an effective amount of an HSV vaccine composition that includes an extract of detergent-treated HSV-infected cells and an adjuvant. In one representative embodiment, HSV is HSV-2. In alternative embodiments, HSV may be, for example, HSV-1 alone or the combination of HSV-2 and HSV-1. In certain embodiments, the virus used to infect cells may include, for example, wild type virus, clinical isolate of virus, recombinant virus, and vectored-expression systems encoding viral proteins, which may be used individually or in combination. In a representative embodiment, the cells are Vero cells. In representative embodiments, the adjuvant may be, for example, alum alone, a combination of MPL and alum, a combination of MPL and TDM, and a combination of MLP, TDM, and biologically-active components of cell wall skeleton. In certain aspects of a representative embodiment, more than one administration is performed over the course of several days, weeks, months, or years to provide initial and continual immunity against HSV. In one aspect, administration of the HSV vaccine composition is achieved intramuscularly (i.m.). Alternatively, administration of the HSV vaccine composition may be achieved, for example, intravenously (i.v.), intradermally (i.d.), subcutaneously (s.q.), or orally. It is contemplated that the HSV vaccine composition may be administered before, after, or simultaneously with at least one other antigen. It is further contemplated that the HSV vaccine composition may be administered with at least one other adjuvant besides that provided as integral to the composition itself.

These and other objects are achieved in the invention.

The present invention fulfills a long felt need in the field of HSV research. The invention overcomes major disadvantages and deficiencies of prior art approaches and current vaccination protocols being developed for the prevention of genital herpes, by providing compositions for vaccinating animals and humans against both HSV-2 and HSV-1 infections and genital herpes as well as for methods of producing and using vaccines against HSV-2 and HSV-1.

There has thus been outlined, rather broadly, features of the invention in order that the detailed description thereof that follows may be better understood, and in order that the present contribution to the art may be better appreciated. There are, of course, additional features of the invention that will be described further hereinafter. Indeed, it is to be understood that both the foregoing general description and the following detailed description are exemplary and explanatory and are intended to provide further explanation of the invention as claimed.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other methods, systems, kits, and compositions for carrying out the several purposes of the present invention. It is important, therefore, that equivalent constructions insofar as they do not depart from the spirit and scope of the present invention, are included in the present invention.

The accompanying drawings are included to provide a further understanding of the invention and are incorporated in and constitute a part of this specification, illustrate several embodiments of the invention, and together with the description serve to explain the principles of the invention.

BRIEF DESCRIPTION OF THE DRAWINGS

FIG. 1A, FIG. 1B, FIG. 1C, FIG. 1D, FIG. 1E, and FIG. 1F show the efficacy and immunogenicity of gD/AS04 vaccine in the cotton rat HSV-2 genital herpes model. Cotton rats were inoculated i.m. with the indicated doses of gD/AS04 vaccine Simplirix™ ("gD") with an interval of 21 days and challenged 6 weeks after the initial immunization with HSV-2, $5 \times 10^4$ PFU per animal following pre-treatment of animals with DMPA 4 days earlier. Control groups included HSV-2-challenged cotton rats inoculated i.m. with PBS, FENDrix™ (a vaccine against hepatitis B), HSV-2 partially inactivated with UV ("UV-HSV"), or PBS-immunized uninfected animals. FIG. 1A shows lesion formation and mortality monitored for 4 weeks after the challenge. Results shown are those of a representative experiment. FIG. 1B depicts a percent disease-free plot of gD/AS04-immunized animals from the experiment described in FIG. 1A. Results are cumulative of two independent experiments, 6-10 animals total per group. Some animals in group vaccinated with gD/AS04 at 0.06 µg recovered from lesions by day 21 of the study, resulting in an apparent increase in percentage of disease-free animals. The asterisk indicates $p<0.05$ compared to the group vaccinated with FENDrix™. FIG. 1C shows HSV-2 viral load quantified by plaque assay on vaginal wash samples collected on day 2 post-infection. Results represent the mean±SE for 4-5 animals per group. The asterisk indicates $p<0.05$ when compared to HSV-2-challenged animals immunized with FENDrix™. For immunogenicity evaluation, serum was collected 21 days after initial immunization (prior to boost), 2.5 weeks after the boost (D38) and 7 days (select groups) after HSV-2 infection and analyzed for neutralization activity (FIG. 1D), gD specific antibody titers by ELISA (FIG. 1E), or reactivity against crude cell extracts from HSV-2 infected cells (FIG. 1F). FIG. 1F includes an insert that shows reactivity of day 38 sera against extracts of control, uninfected Vero cells for the groups shown in the main panel, labeled 1-6 in the order of their appearance. Results are representative of 2 independent experiments with 4-10 samples per group. The asterisk indicates p<0.05 when compared to PBS immunized animals (Boukhvalova et al. 2015. *J Virol* 89(19), 9825-40).

FIG. 2A shows survival curves and FIG. 2B shows viral load in genital tract secretions collected on day 2 post-infection (5-6 animals per group). FIG. 2C shows serum IgG against crude HSV-2-infected cell extract and FIG. 2E shows serum neutralizing antibody levels quantified in samples collected immediately prior to HSV-2 challenge. FIG. 2D shows vaginal wash IgG against crude HSV-2-infected cell extract quantified in samples collected prior to challenge and on days 4 and 7 post-infection. Anti-HSV IgG results represent fold-induction over values detected in PBS-immunized, PBS-challenged animals. Day 7 data for PBS-immunized, HSV-2-challenged group is not available. FIG. 2D includes an insert that shows reactivity of day 7 vaginal wash samples against extracts of control, uninfected Vero cells for the groups shown in the main panel, labeled 1-4 in the order of their appearance. Results are cumulative of two independent experiments. The asterisk indicates p<0.05 when compared to PBS immunized animals (Boukhvalova et al. 2015. *J Virol* 89(19), 9825-40).

FIG. 3A, FIG. 3B, and FIG. 3C show the efficacy of gD/AS04 vaccine in the cotton rat HSV-1 genital herpes model. Cotton rats were inoculated i.m. with the indicated doses of gD/AS04 vaccine Simplirix™ ("gD") with an interval of 21 days and challenged 6 weeks after the initial immunization with HSV-1(17), $2\times10^6$ PFU per animal following pre-treatment with DMPA 4 days earlier. Control groups included HSV-1-challenged cotton rats immunized with FENDrix™, or with HSV-2 partially inactivated with UV ("UV-HSV"). FIG. 3A shows lesion formation and mortality monitored for 4 weeks after the challenge. Results shown are those of a representative experiment. FIG. 3B shows the percent of disease-free animals (lack of lesions and/or mortality) from the experiment described in FIG. 3A. Results are representative of two independent experiments. Some animals in group vaccinated with gD/AS04 at 0.06 ug recovered from lesions by day 28 of the study, resulting in an apparent increase in percentage of disease-free animals. The asterisk indicates p<0.05 compared to FENDrix™-vaccinated animals. FIG. 3C shows HSV-1 viral load quantified by plaque assay on vaginal wash samples collected on day 2 post-infection. Results represent the mean±SE for 5-8 animals per group. The asterisk indicates p<0.05 when compared to HSV-1-challenged animals immunized with FENDrix™ (Boukhvalova et al. 2015. *J Virol* 89(19), 9825-40).

FIG. 4A and FIG. 4B show the efficacy of Vero/HSV vaccine adjuvanted with MPL and TDM (presented as oil-in-water: O/W emulsion), MPL, TDM, and CWS (O/W), MPL with alum or with alum alone. Cotton rats were immunized with the indicated vaccine formulation or with PBS, boosted once i.m. with the same vaccine formulation. After two additional weeks all animals were inoculated with DMPA and 4 days later challenged with HSV-2 (G) at $5\times10^4$ PFU per animal. Clinical signs of disease were monitored for four weeks after infection. Vaginal washes were collected for HSV-2 titration on day 2 post-infection. FIG. 4A depicts lesion formation and mortality monitored for several weeks after infection as described above. FIG. 4B shows HSV-2 load quantified by plaque assay. Results shown are mean±SE for 5-10 animals per group.

DETAILED DESCRIPTION OF THE INVENTION

Figure 1B:
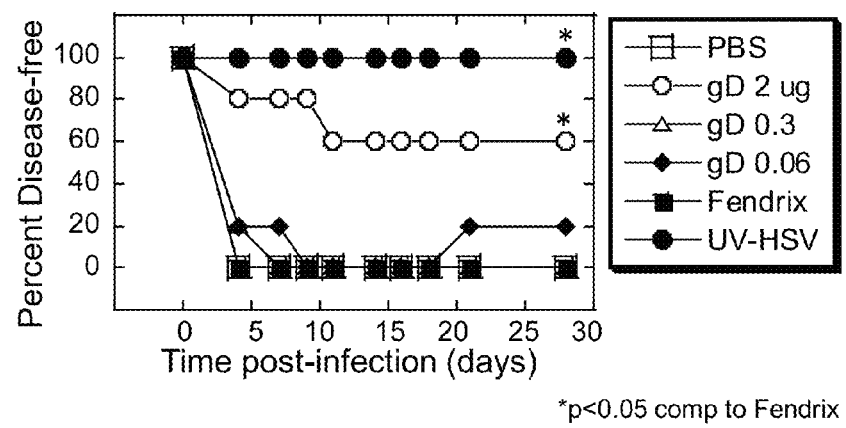

Provided herein are compositions for vaccinating a human or animal against HSV infection. Also provided are methods for producing vaccines against HSV-2 and HSV-1, and using such vaccines against HSV-2 and HSV-1. Reference will now be made in detail to representative embodiments of the invention, examples of which are illustrated in the accompanying drawings.

The majority of preclinical HSV-2 gD-2 vaccine-challenge studies were conducted in Hartley guinea pigs (Bourne N et al. 2003. *J Infect Dis* 187(4), 542-549; Bourne N et al. 2005. *J Infect Dis* 192(12), 2117-2123; Hoshino Y et al. 2005. *J Virol* 79(1):410-8). These studies found that the vaccine elicits strong gD-2-specific ELISA and neutralizing antibody responses in the serum (Belshe R B et al. 2012. *N Engl J Med* 366(1), 34-43). However, although vaccination reduced acute, recurrent and latent HSV-2 infection in guinea pigs (Bourne N et al. 2003. *J Infect Dis* 187(4), 542-549; Bourne N et al. 2005. *J Virol* 79(1):410-8), these outcomes did not translate into protection in the clinical trial. To address this limitation, the gD/AS04 vaccine was evaluated in a cotton rat *Sigmodon hispidus* model of HSV-1 and HSV-2 genital tract disease. This model was selected because studies with other pathogens including polio, adenovirus, RSV, influenza, measles, and rhinovirus indicate that the cotton rat may closely recapitulate human disease (Niewiesk S & Prince G. 2002. *Lab Anim* 36(4):357-72; Boukhvalova M S et al. 2009. *Biologicals* 37(3):152-9; Blanco J C et al. 2013. *J Virol* 87(4):2036-45; Blanco J C et al. 2014. *Trials Vaccinol* 3:52-60). Although the vaccine induced gD-2-specific and HSV-2 neutralizing antibodies in the serum of cotton rats, it provided only partial protection against HSV-2 disease and better protected animals against HSV-1-induced genital herpes with respect to both viral replication and disease. Better protection against HSV-1 compared to HSV-2 disease could also be conferred by passive transfer of serum from gD/AS04-immunized animals (Boukhvalova et al. 2015. *J Virol* 89(19), 9825-40).

Subunit vaccines based on the HSV-2 glycoprotein D (gD-2) have been the major focus of HSV-2 vaccine development for the past two decades. Based on the promising data generated in the guinea pig model, a formulation containing truncated gD-2, aluminum salt, and MPL (gD/AS04) advanced to clinical trials. The results of these trials, however, were unexpected, as the vaccine protected against HSV-1 infection, but not against HSV-2. To address this discrepancy, a Depot medroxyprogesterone (DMPA) treated cotton rat *S. hispidus* model of HSV-2 and HSV-1 genital infection was developed (Boukhvalova et al. 2015. *J Virol* 89(19), 9825-40). Severity of HSV-1 genital herpes was less compared to HSV-2 in cotton rats, yet the model allowed for comparative evaluation of gD/AS04 immunogenicity and efficacy. Cotton rats were intramuscularly vaccinated using a prime boost strategy with gD/AS04 (Simplirix™ vaccine) or control vaccine formulation (hepatitis B vaccine FENDrix™) and subsequently challenged intravaginally with HSV-2 or HSV-1. gD/AS04 vaccine was immunogenic in cotton rats, induced serum IgG directed against gD-2 and serum HSV-2 neutralizing antibodies, but failed to efficiently protect against HSV-2 disease or to decrease HSV-2 viral load. However, gD/AS04 significantly reduced vaginal titers of HSV-1 and better protected animals against HSV-1 compared to HSV-2 genital disease. The latter finding is generally consistent with the clinical outcome of Herpevac trial of Simplirix™. Passive transfer of serum from gD/AS04-immunized cotton rats conferred stronger protection against HSV-1 genital disease. These findings suggest the need for alternative vaccine strategies and the identification of new correlates of protection (Boukhvalova et al. 2015. *J Virol* 89(19), 9825-40).

It is shown herein that gD/AS04 has higher efficacy against HSV-1 compared to HSV-2 genital herpes in the novel DMPA-synchronized cotton rat model of HSV-1 and HSV-2 infection. The findings help explain the results of the Simplirix™ trial and highlight the translational value of the cotton rat model of genital herpes vaccines testing (Boukhvalova et al. 2015. *J Virol* 89(19), 9825-40).

The term "subject" as used herein means, but is not limited to, any animal or human in need of or capable of receiving prophylactic or therapeutic vaccination against HSV-2, HSV-1, HSV-2 and HSV-1, and related disease such as genital herpes.

The term "vaccine" as used herein means, but is not limited to, a formulation or composition that includes live, killed, inactivated, or attenuated microorganisms, or antigenic proteins (or fragments thereof) obtained from microorganisms. In addition, a vaccine is understood to be a formulation or composition that may include disease-associated proteins (or fragments thereof) obtained from microorganisms. The antigenic components of vaccines may be, for example, recombinant or native proteins (or fragments thereof).

The term "vaccination" as used herein means, but is not limited to, the introduction of a vaccine into a subject for the purpose of inducing a protective immune response against a particular disease or disorder (that is, an immunizing procedure in which vaccine is administered to a subject). For example, "vaccination" includes a process which includes the administration of at least one type of HSV vaccine composition (such as disclosed herein) alone or in combination with another antigen and/or adjuvant to an animal or human, whereby the administration elicits an immune response in the animal or human against HSV.

The term "immunization" as used herein means, but is not limited to, the induction of immunity and may include, for example, "active immunization" (which is the stimulation of the immune system to confer protection against a disease or disorder, for example, by administration of a vaccine, toxoid, or microbe) and "passive immunization" (which is where pre-synthesized elements of the immune system (or elements produced in advance), for example, antibodies or cells, are transferred to an animal or human so that the body does not need to produce these elements itself, and occurs physiologically, for example, when antibodies are transferred from mother to fetus during pregnancy or from mother to newborn during lactation and feeding). In some instances, the terms vaccination and immunization may be used interchangeably.

The terms "control," "control sample," and "control agent" as used herein have the meaning ascribed them by a person skilled in the art and mean, but are not limited to, a sample or treatment condition that provides an expected positive or negative result compared to an unknown test sample or treatment, potential vaccine, possible new therapeutic agent, experimental condition, or the like.

The term "immune response" as used herein means, but is not limited to, an integrated response to an antigen involving recognition of antigens by specific antibodies and previously sensitized lymphocytes (adaptive immune response) and by cells of the innate immune system (innate immune response).

The term "antigen" as used herein means, but is not limited to, a live, weakened, or killed microorganism (virus or bacterium), parts of the microorganism (native or recombinant), or disease-associated proteins (or fragments thereof, native or recombinant). The term "antigen" may also mean purified cell extract from cells infected with viruses of the instant invention.

The vaccines, antigens, agents, and adjuvants of the invention may optionally be administered via a delayed-release device or method. The term "delayed-release device or method" as used herein means, but is not limited to, any device or method capable of releasing an agent or product (for example, a drug or a vaccine) at a time later than immediately following its administration. Various delayed-release devices have been described (Stubbe et al. 2004. *Pharm. Res.* 21:1732) and could be applicable to the representative embodiments of the invention. Delayed-release devices and methods can be identified and employed without undue experimentation by one skilled in the art after consideration of all criteria and use of best judgment on the subject's behalf.

The vaccines, vaccine compositions, and agents of the embodiments of the invention are administered in a pharmacologically or physiologically acceptable and effective amount to induce an immune response to an antigen. Similarly, the vaccines, vaccine compositions, and agents of the embodiments of the invention are administered in prophylactically or therapeutically effective amounts, which are to be understood as amounts meeting the intended prophylactic or therapeutic objectives, and providing the benefits available from administration of such vaccines, vaccine compositions, and agents.

The term "effective amount" as used herein means, but is not limited to, a concentration capable of inducing humoral immunity, cell-mediated immunity, or a combination of humoral and cell-mediated immunity in a subject, which is sufficient to cure (partly or completely) or prevent disease or disorder caused by an antigen (including, for example, herpes simplex virus). For example, an effective amount of vaccine refers to the amount administered to achieve seroconversion and is evidenced such as by the presence of, for example, a two- to four-fold higher level of antigen-specific antibodies in the subject's serum. One skilled in the art would understand the range of immunological responses anticipated by the terms "humoral immunity" and "cell-mediated immunity," such as antibody production and activities, T cell proliferation and activities, and cytokine production and activities. Effective amount is understood to be an amount not harmful to the subject where any harmful side effects are outweighed by the benefits.

In general, the dosage ranges for administration of the vaccines, vaccine compositions, and agents according to the present invention are those that produce the desired effect(s). The useful dosage to be administered will vary depending on the age, weight, and type of subject vaccinated, the mode, route, and schedule of administration, the response of the individual subject, and the type of pathogen/antigen against which vaccination is sought. The dosage will also vary with the nature or the severity of the underlying condition, with epidemiologic conditions, with the concomitant use of other active compounds, and the route of administration. In addition, the dosage will be determined by the existence of any adverse side effects such as local hypersensitivity, systemic adverse effects, and immune tolerance.

An effective dose of the vaccine (and other agent(s)) can be determined without undue experimentation (for example, by pharmacokinetic studies) by one skilled in the art after consideration of all criteria and use of best judgment on the patient's behalf (and will most often be contingent upon the particular vaccine composition utilized). The dosage to be administered will depend upon the particular case, but in any event, it is the amount sufficient to induce a protective antibody and/or cell-mediated immune response against herpes simplex virus.

Optionally, one or more compounds having adjuvant activity may be added to the vaccines or vaccine compositions of the invention. The term "adjuvant" as used herein means, but is not limited to, a non-specific stimulator of the immune system. Adjuvants enhance the immune response of the host to the vaccine. Examples of adjuvants known in the art are Freund's Complete and Incomplete adjuvant, agonists of Toll-like receptors, RIG-like receptors, other receptor molecules, vitamin E, non-ionic block polymers, muramyl dipeptides, immune stimulating complexes, saponins, mineral oil, vegetable oil, and Carbopol. Adjuvants, especially suitable for mucosal application are, for example, the *E. coli* heat-labile enterotoxin (recombinant or otherwise) and Cholera toxin. Other suitable adjuvants are, for example, aluminum hydroxide, aluminum phosphate or aluminum oxide, oil-emulsions (for example, of Bayol F.sup.(R) or Marcol 52.sup.(R)), and vitamin-E solubilisate. Other adjuvants can include, for example, GPI-0100 (Galenica Pharmaceuticals, Inc., Birmingham, Ala.), water-in-oil emulsion, oil-in-water emulsion, or water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (for example, anhydromamiitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. A further instance of an adjuvant is a compound chosen from the polymers of acrylic or methacrylic acid and the copolymers of maleic anhydride and alkenyl derivative. Other adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, and IMS 1314, among many others. In representative embodiments of the invention, adjuvants may be, for example, alum, monophosphoryl lipid A (MPL) in combination with alum, and/or MPL and biologically-active components based on mycobacterial products (including, for example, trehalose 6, 6'-dimycoloate (TMD) and cell wall skeleton).

The vaccines, vaccine compositions, and agents of the embodiments of the invention may, optionally, be administered in combination with (or may include) one or more pharmaceutically acceptable carriers, diluents, or excipients. Vaccines, vaccination techniques, pharmaceutical compositions, methods of preparing pharmaceutical compositions, and pharmaceutically acceptable carriers, diluents, and excipients are known in the art and are described, for example, in "*Remington: The Science and Practice of Pharmacy*" (formerly "*Remington's Pharmaceutical Sciences*," University of the Sciences in Philadelphia, Lippincott, Williams & Wilkins, Philadelphia, Pa. (2005)), the disclosure of which is hereby incorporated by reference. A person skilled in the art may use known injectable, physiologically acceptable sterile solutions. For preparing a ready-to-use solution for parenteral injection or infusion, aqueous isotonic solutions, for example, saline, phosphate buffered saline (PBS) or corresponding plasma protein solutions, are readily available. The vaccine compositions may be present as lyophylisates or dry preparations, which can be reconstituted with a known injectable solution directly before use under sterile conditions, for example, as a kit of parts. In addition, the immunogenic and vaccine compositions of the present invention can include one or more acceptable carriers (which may include, for example, solvents, dispersion media, coatings, adjuvants, stabilizing agents, diluents, preservatives, antibacterial and antifungal agents, isotonic agents, adsorption delaying agents, and the like. "Diluents" can include water, saline, PBS, dextrose, ethanol, glycerol, and the like. Isotonic agents can include sodium chloride, dextrose, mannitol, sorbitol, and lactose, among others. Stabilizers include albumin and alkali salts of ethylenediaminetetracetic acid, among others.

Any suitable route of administration may be employed for providing a subject with an effective amount/dosage of vaccine, vaccine composition, and agents according to the representative embodiments of the invention. A suitable route of administration may be determined readily by one skilled in the art of pharmacology, immunology, medicine, or the like without undue experimentation. For example, the dosage may be administered orally, intranasally (i.n.), parenterally, topically, intravenously (i.v.), intraoccularly, by injection, subcutaneously (s.q.), or the like. It is understood that injection comprises also perfusion and continuous infusion. Dosage forms may include, for example, tablets, capsules, powders, solutions, dispersions, suspensions, ointments, and aerosols.

The term "cell wall skeleton" as used herein means, but is not limited to cell wall skeleton from tubercule bacillus. Cell wall skeleton may include, for example, whole cell wall skeleton, biologically-active components of cell wall skeleton, and/or synthetic analogues of cell wall skeleton.

"TDM" may include, for example, whole TDM, biologically-active components of TDM, and/or synthetic analogues of TDM.

The term "biologically-active components" as used herein has the meaning ascribed to it by persons of skill in the art and may be further defined herein as components with adjuvant properties. Biologically-active components and synthetic analogues of cell wall skeleton and TDM may include, for example, N-acetylmuramyl-1-alanyl-D-isoglutamine (MDP), threonyl-MDP, muramyl tripeptide, murabudite, and trehalose-6,6'-dibehenate (TDB).

"MPL" may include, for example, whole MPL, biologically-active components of MPL, and/or synthetic analogues of MPL. MPL may be, for example, *Salmonella minnesota* MPL.

The term "oil-in-water emulsion (O/W)" as used herein means, but is not limited to, the combination of squalene oil, 0.2% Tween 80, and water.

The term "detergent" as used herein means, but is not limited to, the class of molecules whose unique properties enable, for example, lysing of cells (and resulting release of soluble proteins), solubilizing of membrane proteins and lipids, and other actions well known to one skilled in the art. Detergents include, for example, nonionic, anionic, zwitterionic, denaturing, and nondenaturing detergents. The term "IGEPAL" as used herein means IGEPAL CA-630 (octylphenoxypolyethyleneoxyethanol, which is a branched, nonionic, non-denaturing detergent).

The terms "purify," "purified," and "purification" as used herein have the meaning ascribed them by a person skilled in the art and mean, but are not limited to, a series of processes intended to isolate one or a few proteins from a complex mixture, such as cells, tissues, whole organisms, or extracts thereof. One skilled in the art readily understands and can select without undue experimentation the various means of protein (including antigen) purification. When used herein, the terms may include various degrees ranging from partial to complete.

The terms "extract," and "cell extract" as used herein have the meaning ascribed them by a person skilled in the art and mean, but are not limited to, material derived from lysed cells that has been subjected to various degrees of purification including, for example, centrifugation to remove insoluble matter and dialysis to enrich for molecules of a particular weight or range of molecular weights.

The following examples are provided for illustration purposes only, and are in no way intended to limit the scope of the present invention.

Example 1

Materials and Methods
Cells and Virus
HSV-2(G) and HSV-1(17) were grown on Vero cells and stored at −80° C. at a concentration of ~$10^8$ PFU/ml. Viruses were diluted in PBS, pH 7.4 to the appropriate concentration within an hour of infection and maintained on ice.

Reagents and Vaccines
Depot medroxyprogesterone acetate (DMPA) as an injectable suspension (DepoProvera 150 mg/ml, GreenStone NDC 59762-4537-1) was obtained from Blue Door Pharma. gD/AS04 vaccine (each 0.5 ml vaccine dose contains 20 μg gD-2 antigen, 50 μg MPL, and 500 μg alum), FENDrix™ vaccine (each 0.5 ml dose contains 20 μg Hepatitis B surface antigen, 50 μg MPL and 500 μg alum), and recombinant gD-2 antigen for ELISA (375 μg/ml) were kindly provided by GlaxoSmithKline Vaccines. Partially-inactivated HSV-2 was prepared by exposing $10^8$ PFU/ml of HSV-2(G) to ultraviolet light for 2 min (UV-HSV). Completely-inactivated HSV-2 was prepared by exposing the virus to a 63° C. water bath for 30 minutes (heat-inactivated (HI-HSV)). The UV-treated virus had a reduction of infectious titer from $10^8$ PFU/ml prior to inactivation to ~$10^6$ PFU/ml and the heat-inactivated virus had no detectable infectivity in $TCID_{50}$ assay on Vero cells.

Animals
Inbred *S. hispidus* cotton rats were obtained from a colony maintained at Sigmovir Biosystems, Inc. Six to eight-week old female cotton rats were used for the studies. Animals were housed in large polycarbonate cages and were fed a standard diet of rodent chow and water. The colony was monitored for antibodies to adventitious respiratory viruses and other common rodent pathogens and no such antibodies were found. All studies were conducted under applicable laws and guidelines and after approval from the Sigmovir Biosystems, Inc.'s Institutional Animal Care and Use Committee (IACUC).

Animal Studies
Animal studies were repeated at least once, with results of representative experiments shown.

Vaccine Studies
Cotton rats were anesthetized with isoflurane, pre-bled, and inoculated i.m. into a hind leg with 100 μl of gD/AS04 vaccine at 2 μg, 0.3 μg or 0.06 μg (corresponding to 1:2, 1:12, and 1:72 dilution of gD/AS04 for both antigen and adjuvants) per animal (~100 g body weight). Control groups of animals were immunized i.m. with 100 μl of FENDrix™ (1:2 dilution of vaccine) or 100 μl of PBS, pH 7.4 per 100 g body weight. UV-HSV or HI-HSV was administered as an i.m. injection of virus solution corresponding to an infectious dose of $10^5$ PFU per animal prior to inactivation. Three weeks later, animals were eye bled and boosted with the same vaccine formulation as given on day 0. Three weeks following the booster vaccination, animals were eye bled and vaginal washes were collected using 400 μl PBS and stored at −80° C. Vaccine subject to the invention described herein (Vero/HSV+alum, Vero/HSV+MPL+alum, Vero/HSV+MPL+TDM, Vero/HSV+MPL+TDM+CWS, Vero/HSV) were administered i.m. or s.c. as 100 μl per animal (~100 g body weight) with an interval of 2-3 weeks before priming and boosting and between boosting and DMPA treatment. The animals were inoculated s.c. with DMPA (50 μl of 15 mg/ml per 100 g animal) and four days later inoculated intravaginally with $5\times10^4$ PFU HSV-2 or $2\times10^6$ PFU HSV-1 per animal under ketamine/xylazine anesthesia. Lesion formation and mortality after infection were monitored for several weeks, with differences between groups evaluated by Log-rank Test. Animals of morbid appearance were euthanized. Samples for viral titrations were collected by washing the vaginal tract of animals with EMEM/gentamicin/fungizone/sucrose as described above. Follow-up studies with HI and UV-treated virus were conducted following the same immunization protocol except the interval between primary vaccination and boost was 2 weeks, followed by 2.5 weeks between boost and HSV-2 challenge to accommodate a shorter experimental frame.

Virus Titrations
Vaginal washes were assayed for the presence of infectious HSV by titering on Vero cells by plaque assay. In brief, vaginal washes were clarified by centrifugation and diluted in EMEM. Confluent Vero monolayers were infected in duplicate with diluted homogenates in 24-well plates. After one-hour incubation at 37° C. in a 5% $CO_2$ incubator, cells were overlaid with 0.75% methylcellulose medium. After 2 days of incubation, the overlay was removed and the cells were fixed with 0.1% crystal violet stain for one hour and then rinsed and air dried. Plaques were counted and virus titer was expressed as PFU/ml of vaginal wash, with differences between groups evaluated by Student t-test.

Preparation of Extracts of HSV-2-Infected Cells for ELISA

Vero cells were propagated in EMEM supplemented with 10% FBS, L-glutamine, gentamicin, and fungizone and infected at subconfluency with HSV-2 at MOI of 0.01. After 18 hrs of infection, cells were washed with 10 ml Tris-NaCl buffer (50 mM Tris-HCl pH7.5, 100 mM NaCl) with 2 mM EDTA and lysed on ice in-flask with 1% IGEPAL in Tris-NaCl buffer supplemented with 0.2 mM PMSF. Cell solution was collected into a pre-chilled 50 ml conical tube, subjected to one cycle of freeze-thaw, and centrifuged for 15 min at 4,000 g at 4° C. Supernatants were filtered through the 70 µM nylon sieve and centrifuged for 30 min at 4,500 rpm at 4° C. The protein solution was transferred to a SnakeSkin Pleated Dialysis Tubing (Pierce, 10,000 MWCO) and dialyzed against 2 changes of PBS, pH 7.4 at 4° C. The dialyzed solution was cleared by an additional centrifugation for 30 min at 4,000 g at 4° C., aliquoted and stored at −80° C. until use. Extracts of mock-infected Vero cells were prepared following the same protocol, with the only exception that no virus was used during infection step.

ELISA for gD-2 and Total HSV-2 Antigens

ELISA for gD-2-specific IgG was performed on 96-well Immulon B microplates coated with 1 µg/ml recombinant gD-2 (provided by GSK). Serum IgG was detected with chicken anti-cotton rat IgG (Immunology Consultants Laboratory) at 0.4 µg/ml, followed by an HRP-conjugated goat anti-chicken IgG (KPL) at 50 ng/ml. The signal was detected with SureBlue TMB substrate (KPL). The amount of anti-gD-2 IgG in each sample was calculated based on the standard curve of serially-diluted serum collected from animals immunized with 2 µg gD/AS04 twice (gD-2 ELISA serum standard), with the amount of anti-gD-2 IgG in 1:500 dilution of standard serum sample equal to 1,000 Units.

For total HSV-2 protein ELISA, the plates were coated with the extracts from HSV-2 infected Vero cells diluted 1:500 in coating buffer (KPL). Chicken anti-cotton rat IgG and HRP-conjugated goat anti-chicken IgG were used at 0.4 µg/ml and 50 ng/ml, respectively. Signal was detected using SureBlue TMB substrate. The amount of anti-HSV IgG in each sample was calculated based on the standard curve obtained with sera from animals vaccinated twice with UV-HSV i.m. (total HSV-2 protein ELISA serum standard), with the amount of anti-HSV IgG in 1:500 dilution of standard serum sample equal to 1,000 Units. Assay conditions for total HSV-2 protein ELISA were optimized by testing total HSV-2 protein ELISA serum standard sera on plates coated with extracts of HSV-2- or mock-infected Vero cells. Assay conditions minimizing background reading arising from wells coated with mock-infected cells were selected. All experimental sera or vaginal wash samples were tested in duplicate.

Neutralizing Antibody Assay

Serial dilutions of serum or vaginal washes were mixed with $10^5$ PFU/ml of HSV-2, incubated for 1 h at 24° C. and inoculated onto subconfluent monolayers of Vero cells in 96-well plates. After 1 h incubation, the inoculum was removed, cells washed with PBS, overlaid with EMEM supplemented with 10% FBS, L-glutamine, gentamicin, and fungizone and returned to the incubator for 24 hrs. Neutralizing titer was expressed as the reciprocal of the highest dilution of serum at which the infectivity was completely neutralized (no cytopathic effect visible) in 50% of the wells.

Example 2

Efficacy of gD/AS04 Vaccine Against HSV-2 Genital Herpes in DMPA-Synchronized Cotton Rats *S. Hispidus*

To investigate gD/AS04 efficacy in the HSV-2 challenge model, female cotton rats were immunized intramuscularly with different doses of gD/AS04 twice with an interval of 21 days between the doses and between the second dose and DMPA treatment and then 4 days later intravaginally challenged with $5 \times 10^4$ PFU HSV-2 per animal. gD/AS04 vaccine doses ranged from 0.06 to 2 µg per animal. PBS- or FENDrix™-immunized animals served as a negative control.

Figure 1C:
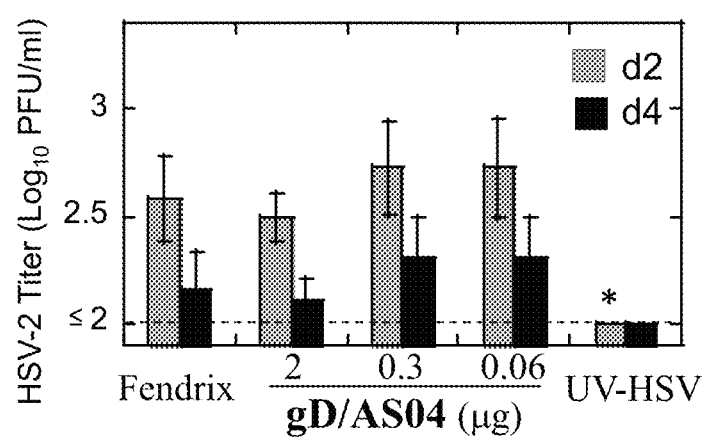

All of the PBS or FENDrix™ treated animals succumbed to HSV-2 disease whereas gD/AS04 provided no protection at the lowest doses (0.06 and 0.3 µg/ml) tested but provided partial protection (2/5 cotton rats had no lesions) from disease when administered at the highest dose of 2 µg per animal (FIG. 1A). This high dose of vaccine protected ~50-60% of immunized animals against mortality in two independent studies. Notably, two of the gD/AS04-immunized animals (90644 and 90651) developed lesions but then recovered. In contrast, all of the PBS- or FENDrix™-immunized animals died shortly after lesion onset. For comparison to efficacy against HSV-1 genital herpes, efficacy against HSV-2 disease was expressed as percentage of disease-free animals that were alive and not showing a lesion at the time of analysis (FIG. 1B), and was found to be significant only for the 2 µg vaccine dose. There were no differences in the amount of HSV-2 shed in vaginal washes in the gD/AS04 immunized cotton rats (FIG. 1C).

UV-treated virus administered at a dose equivalent to $10^3$ PFU per animal (corresponding to original $10^5$ PFU per animal formulation prior to UV exposure) administered in a prime-boost regimen conferred 100% protection against lesion formation and mortality (FIG. 1A and FIG. 1B). All animals immunized with UV-HSV survived vaginal challenge. No virus was recovered from vaginal washes of HSV-2-infected animals immunized with UV-HSV (FIG. 1C). Completely inactivated HSV (HI-HSV) provided partial protection similar to that observed with gD-2 subunit vaccine, suggesting the need for at least some active viral gene expression to achieve full protection (Boukhvalova et al. 2015. *J Virol* 89(19), 9825-40).

Example 3

Immunogenicity of gD/AS04 Vaccine in the Cotton Rat Model

Figure 1D:
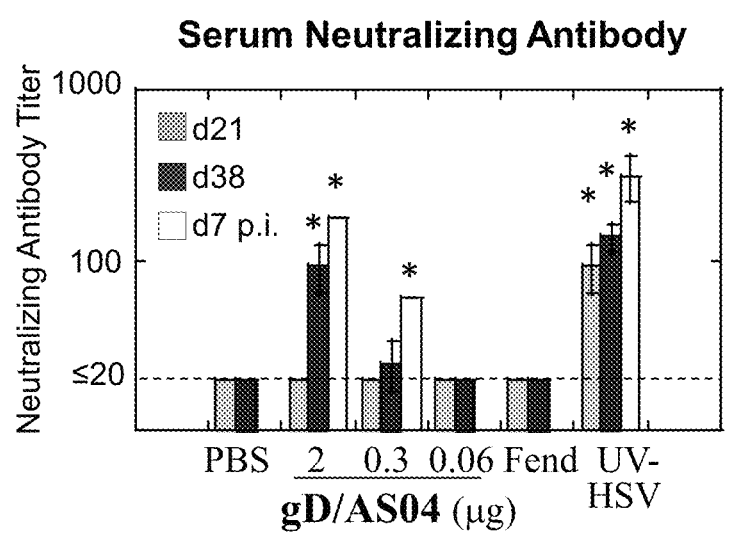
Figure 1E:
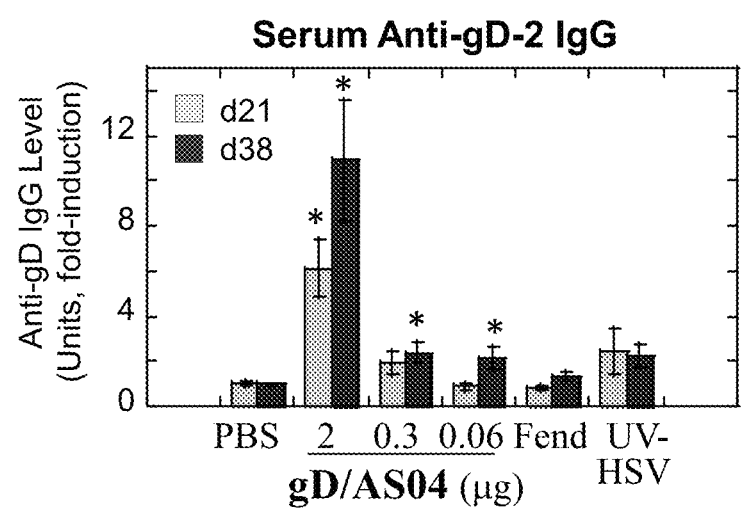
Figure 1F:
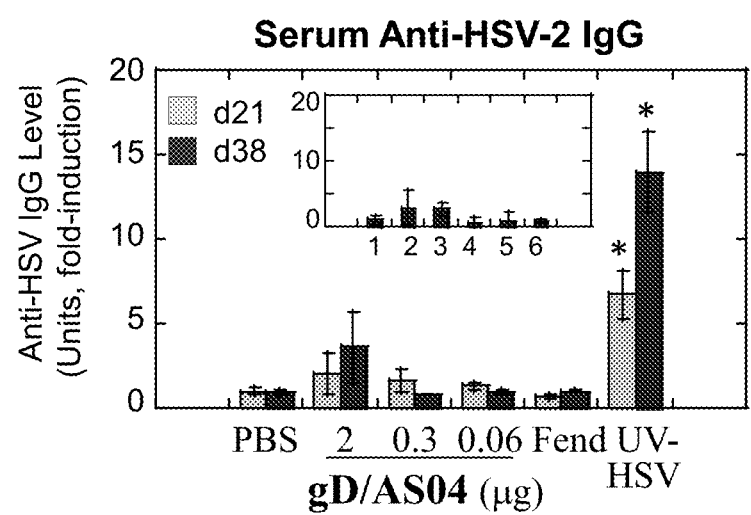

To investigate antibody responses to gD/AS04 immunization in cotton rats, serum was collected at various time points of the experiment: 3 weeks after priming, two weeks after the boost, and one week after intravaginal challenge. gD/AS04 immunization induced a strong dose-dependent serum neutralizing antibody response and increase in gD-2-reactive IgG in cotton rat serum (FIG. 1D). Serum anti-gD-2 IgG levels increased significantly after the first dose of gD/AS04, while neutralizing antibody response to gD/AS04 required priming and boosting with gD/AS04. gD/AS04 vaccine induced significantly higher (approximately 5-fold difference) levels of gD-2-specific IgG compared to UV-HSV-immunization, although the latter induced a strong neutralizing antibody response against HSV-2. The low level of ELISA binding antibodies reactive with recombinant gD-2 in animals immunized with UV-HSV was surprising and suggested that the recombinant protein used for immunization could be immunologically different from the native HSV-2 glycoprotein D and/or that antibodies to other proteins contribute to neutralizing activity. Consistent with this notion, higher levels of antibodies reactive with crude lysates of HSV-2 infected cells were observed in serum of animals immunized with UV-HSV compared to gD/AS04 (FIG. 1F) (Boukhvalova et al. 2015. *J Virol* 89(19), 9825-40).

Figure 2A:
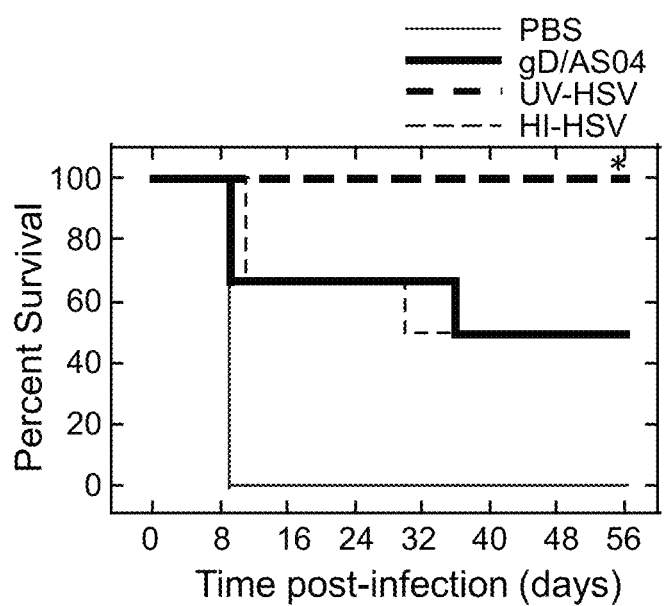
FIG. 2A, FIG. 2B, FIG. 2C, FIG. 2D, and FIG. 2E define correlates of protection in the cotton rat HSV-2 vaccine model. Efficacy and immunogenicity of heat-inactivated HSV-2 (HI-HSV), UV-treated HSV-2 (UV-HSV), and gD/AS04 (2 µg gD-2 antigen, 5 µg MPL, and 50 µg alum) were compared. Animals were immunized with appropriate formulation, boosted 2 weeks later, and infected 2.5 weeks after the boost.
Figure 2B:
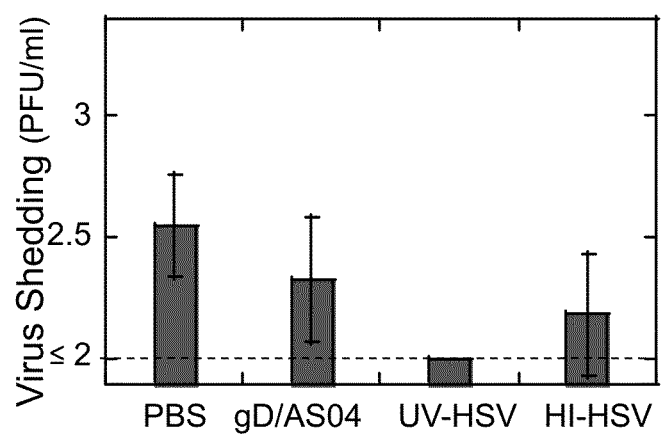
Figure 2C:
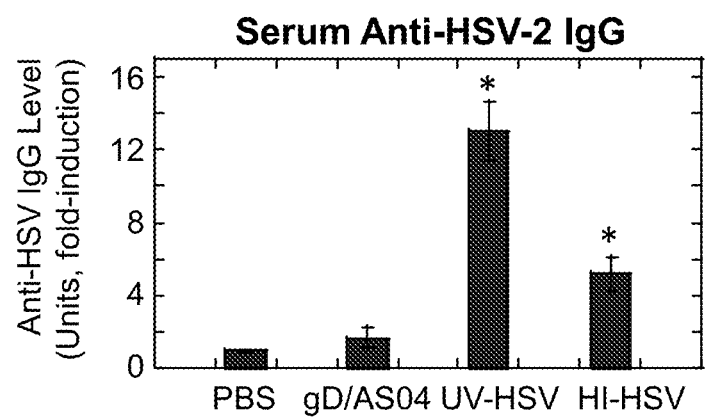
Figure 2D:
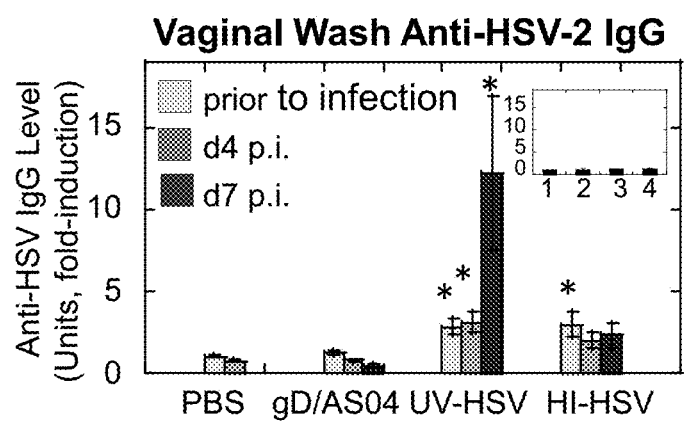
Figure 2E:
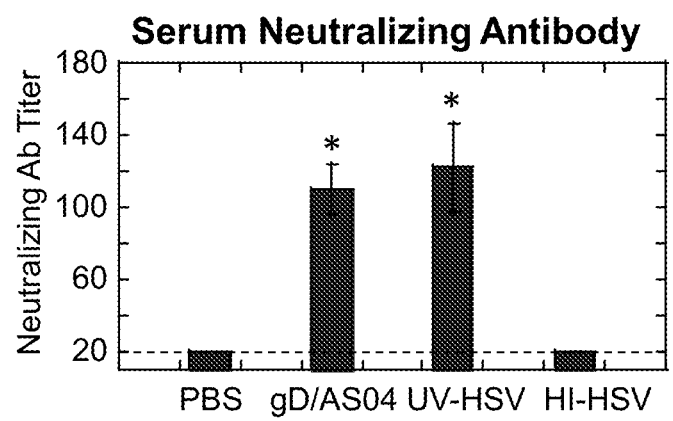

To further investigate correlates of protection, immunogenicity of UV-HSV, HI-HSV and gD/AS04 (2 μg) were compared in a follow-up study. The UV-HSV again completely protected against disease and reduced the amount of virus detected in vaginal washes (FIG. 2A and FIG. 2B). HI virus induced an increase in IgG reactive with infected cell lysates in the serum and vaginal washes (FIG. 2C and FIG. 2D), but failed to induce neutralizing antibody responses (FIG. 2E). The UV-treated virus induced the highest levels of anti-HSV-2 IgG in both the serum and vaginal washes obtained prior to challenge and 4 and 7 days post-infection (FIG. 2D). No anti-gD-2 or neutralizing antibodies were detected in vaginal washes under the conditions tested (Boukhvalova et al. 2015. *J Virol* 89(19), 9825-40).

Example 4

Efficacy of gD/AS04 Vaccine Against HSV-1 Genital Herpes in Cotton Rats S. *Hispidus*

Figure 3B:
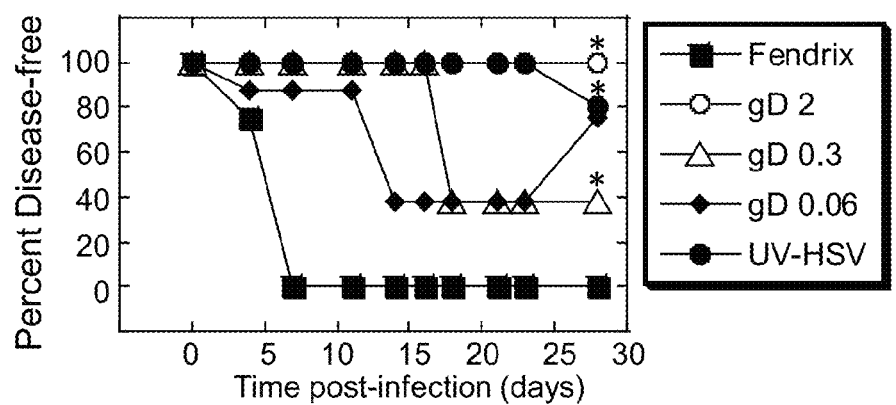
Figure 3C:
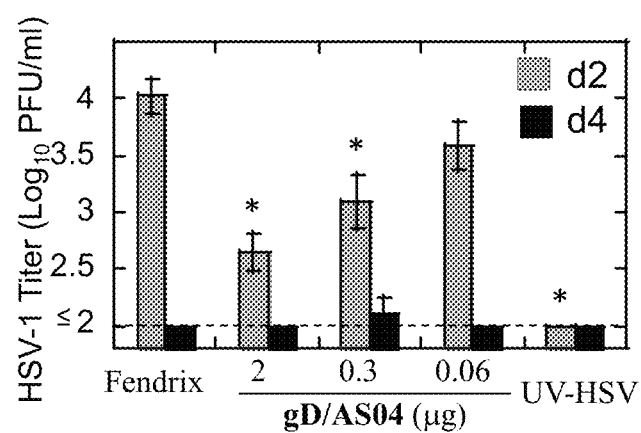

To determine whether gD/AS04 vaccine protected against HSV-1 genital herpes, animals were vaccinated with gD/AS04 using the same experimental protocol as for HSV-2 and challenged intravaginally with HSV-1 at $2\times10^6$ PFU/animal. All animals vaccinated with 2 μg gD/AS04 were completely protected against HSV-1 disease whereas all control animals developed genital herpes (FIG. 3A). Intermediate vaccine dose of 0.3 μg gD/AS04 also induced significant protection by delaying lesion onset by ~2 weeks and reducing disease-associated mortality, resulting in a significant increase in the number of disease-free animals compared to FENDrix™-immunized group (FIG. 3B) (significant protection against HSV-1 disease induced by vaccination with 0.3 and 2 μg gD/AS04 was confirmed by a second independent study). Protection was accompanied by a dose-dependent reduction in viral replication in vaginal wash samples (FIG. 3C), which was also significant for the highest and intermediate vaccine doses (also confirmed by the second study). Viral load was reduced by ~1.5 $\log_{10}$ and 1 $\log_{10}$ in animals vaccinated with 2 μg or 0.3 μg gD/AS04, respectively, compared to FENDrix™-vaccinated animals. Immunization with UV-HSV-2 protected 80% of animals from signs of disease and reduced HSV-1 replication to undetectable levels (FIG. 3A, FIG. 3B, and FIG. 3C). Overall, significant protection against HSV-1 genital herpes was achieved by the highest and intermediate gD/AS04 doses, which also caused significant reduction in vaginal viral load. For HSV-2, only the highest vaccine dose induced statistically-significant (albeit partial) protection against HSV-2 disease and no antiviral efficacy was seen for any of the vaccine doses (Boukhvalova et al. 2015. *J Virol* 89(19), 9825-40).

As disclosed herein, the gD/AS04 vaccine induced serum IgG directed against gD-2 and serum HSV-2 neutralizing antibodies but failed to reduce HSV-2 viral load. It was also found that gD/AS04 provided better protection against HSV-1 than HSV-2 disease. These findings are generally consistent with the results of the Herpevac clinical trial and follow up analysis of its participants (Bernstein D I et al. 2013. *Clin Infect Dis* 56(3):344-51; Belshe R B et al. 2012; *N Engl J Med* 366(1), 34-43; Stanberry L R et al. 2002. GlaxoSmithKline Herpes Vaccine Efficacy Study Group. *N Engl J Med* 347(21), 1652-1661). Moreover, although HSV-1 load was not evaluated in the Herpevac trial, the results herein suggest that gD/AS04 vaccination can diminish HSV-1 vaginal titers. The doses of vaccine that significantly improved HSV-1 disease outcome also caused significant decline in viral load in vaginal secretions of HSV-1-infected cotton rats.

In the process of defining correlates of immunity to HSV-2, a "positive control" immunization strategy was identified using partially inactivated HSV-2 treated briefly with UV light. Intramuscular immunization of cotton rats with UV-HSV-2 (remaining infectious titer $10^3$ PFU per animal) protected 100% of animals against HSV-2 disease and infection. Importantly, UV-HSV immunization induced only low levels of antibodies against recombinant gD-2, but comparable to gD/AS04 levels of neutralizing antibodies and high levels of antibodies reactive with lysates of HSV-2-infected cells. These findings suggest that the UV-HSV-2 elicited antibodies that recognize different neutralizing epitopes within glycoprotein D or induced neutralizing antibodies against other viral proteins.

Although subsequent clinical trials did not confirm protection against HSV-2, they did show that serum gD-2 antibodies and HSV-2 neutralizing antibodies against HSV-2 were induced by gD/AS04 vaccine in human subjects (Stanberry L R. 2004. *Herpes* 11 Suppl 3, 161A-169A; Belshe R B et al. 2012. *N Engl J Med* 366(1), 34-43). Findings presented here suggest that gD-2-specific serum antibodies are not a correlate of protection against HSV-2, which is consistent with the clinical trial outcome. Antibodies against gD-2 in cotton rats, however, may provide a correlate of protection against HSV-1, similar to recently reported finding in humans (Saba E et al. 2010. *Mucosal Immunol* 3:280-290). Results presented herein also suggest that serum neutralizing antibodies, which are commonly used as correlates of protection in pre-clinical and early clinical evaluations of vaccine candidates, are not the sole predictors of HSV-2 vaccine candidate efficacy. The gD/AS04 vaccine, but not HI virus, induced significant serum neutralizing antibodies, yet both gD/AS04 and HI-HSV provided similar levels of protection. Conversely, the UV-HSV and gD/AS04 vaccine induced similar levels of serum neutralizing antibodies, but only the UV-HSV was fully protective. Notably, immunization with UV-treated virus was associated with the highest levels of HSV-specific IgG antibodies in vaginal washes. The levels increased following vaginal challenge, which may have contributed to the strong antiviral effect.

Immune mechanisms responsible for higher efficacy of partially compared to completely inactivated HSV-2 warrant further investigation. Intracellular production of proteins and nucleic acids by replicating virus may engage intracellular pattern recognition receptors and enhance immunogenicity, while expression of non-structural proteins may be required to provide important antigens. Engagement of T cell immunity by virus retaining partial replicative ability might also be of importance for effective protection against HSV-2 (Laing K J et al. 2012. *Clin Exp Immunol* 167(1): 47-58). Herein, we disclose and claim representative embodiments of HSV vaccine compositions containing a variety of HSV proteins expressed in infected cells.

Example 5

Efficacy of Adjuvanted Vaccine Against HSV Infections Based on Extracts of Detergent-Treated HSV-Infected Vero Cells As discussed above, genital herpes caused by HSV-2 or HSV-1 is a debilitating disease that also predisposes individuals to acquisition of HIV. Despite a long-felt need in the art and numerous attempts to fulfill the need, an effective vaccine against genital herpes is remains unavailable. Indeed, the failure of HSV-2 vaccine gD/AS04 showed that alternative approaches to HSV vaccine development are needed. The above studies using cotton rats confirmed the general features of the failed gD/AS04 trials while simultaneously highlighting the translational value of the cotton rat model for vaccine research (Boukhvalova et al. 2015. *J Virol* 89(19), 9825-40).

As a part of the studies described above, it was discovered that efficient protection against genital herpes in cotton rats can be dependent on a broad polyvalent response against multiple HSV proteins contained in extracts of Vero cells infected with HSV-2 (Vero/HSV). These extracts were originally prepared for use in ELISA by detergent disruption of HSV-2-infected Vero cells, subjected to freeze-thaw cycle, low-speed centrifugation, sieve filtration, and dialysis. However, Vero/HSV extracts have been tested as a vaccine in a series of experiments which demonstrated that when properly adjuvanted, Vero/HSV becomes a highly efficient and safe vaccine against herpes infection. In particular, including adjuvants like alum, MPL, TDM, or CWS appears to be required for the efficient HSV vaccine.

Figure 4B:
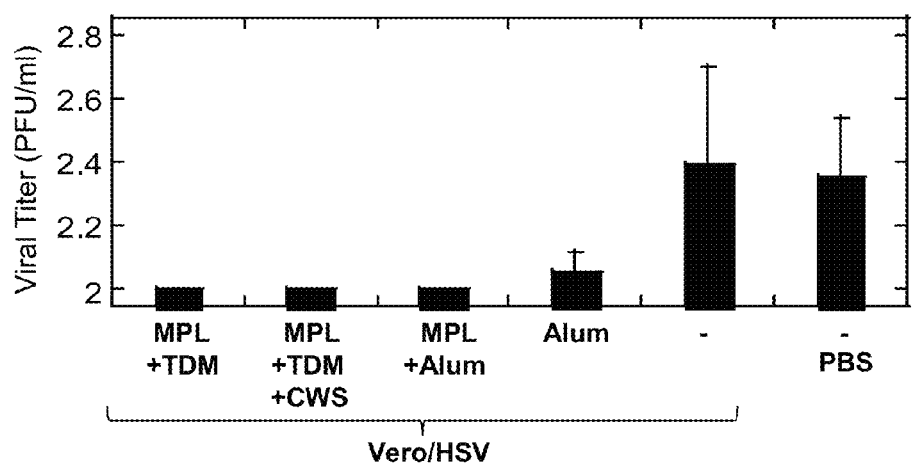
Figure 5:
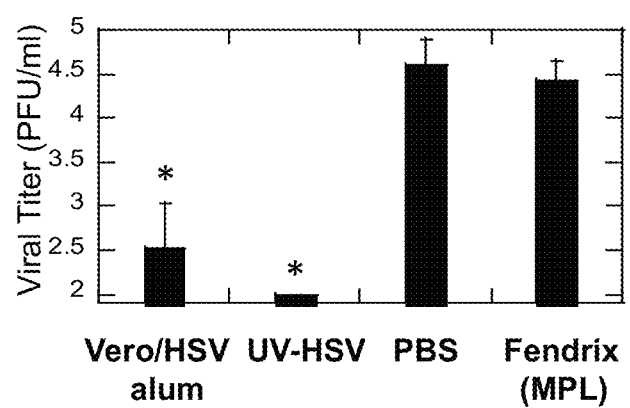
FIG. 5 shows the efficacy of Vero/HSV vaccine against HSV-1 infection. Cotton rats were immunized with Vero/HSV extracts (the same extracts as shown in FIG. 4, prepared from HSV-2 infected cells) adjuvanted with alum, with UV-HSV (HSV-2 stock preparation partially inactivated with UV light), with PBS, or with hepatitis vaccine FENDrix™ adjuvanted with MPL and alum. Three weeks later animals were boosted with the same formulation and after two additional weeks all animals were inoculated with DMPA and 4 days later challenged with HSV-1 (17) $2\times10^6$ PFU per animal. Vaginal washes were collected for HSV-1 quantification by plaque assay on day 2 post-infection. Vero/HSV extracts adjuvanted with alum induced significant protection of cotton rats against HSV-1 replication, only slightly weaker than that induced by UV-HSV. Results shown are mean±SE for 5-10 animals per group.

As shown in FIG. 4A and FIG. 4B, addition of alum, MPL with alum, or MPL with mycobacterial components, such as TDM or TDM and CWS, significantly increased the efficacy of Vero/HSV extracts and in some cases resulted in 100% protection of animals against HSV-2 genital herpes. Furthermore, Vero/HSV prepared from cells infected with HSV-2 induced strong antiviral protection against HSV-1 genital herpes (FIG. 5), suggesting that the vaccine would be efficacious against both HSV-2 and HSV-1 genital herpes. Vero cells will be used for HSV vaccine production as an approved cell substrate utilized in manufacturing of multiple vaccines, including polio, rabies, and smallpox vaccines (Barret et al., *Expert Review Vaccines*, 2009).

Example 6

Preparation of HSV Vaccine Antigen

Based on results described above, the following methods have been developed to prepare a vaccine against HSV-2 and HSV-1 infections using detergent-extracted lysates of infected Vero cells adjuvanted with alum alone, combination of alum and MPL, and/or combinations of MPL with mycobacterial component(s) in water in oil (W/O) emulsion. A representative vaccine of this invention, Vero/HSV (containing extracts of detergent-treated HSV-infected Vero cells) is compared to the so-called "Skinner vaccine" (see Table I). The Skinner vaccine was prepared by detergent disruption of serum-starved, HSV-1-infected MRC5 cells subjected to formaldehyde treatment, acetone precipitation/sucrose fractionation, and adjuvanted with alum. Skinner vaccine was tested in clinical trials and was found to be safe and immunogenic, but its further development was abandoned because no consistent improvement in disease outcome could be shown. The unexpected and superior results shown above using the vaccine compositions of the instant invention suggest that the Skinner vaccine failed to deliver consistent performance because alum alone was used as an adjuvant and because there were flaws in the Skinner vaccine formulation.

The vaccine compositions of the instant invention are significantly different from the Skinner vaccine (Table I). The vaccine compositions here use Vero cells instead of MRC5 cells as a cell substrate, and infection in the case of the instant vaccine compositions is performed at a much lower viral multiplicity of infection (MOI) to reduce the potential production of defective interfering particles. Additionally, although the vaccine compositions of the instant invention are moderately efficacious when alum alone is used as an adjuvant, they exhibit unexpected superior efficacy when MPL is present in the adjuvant formulation. The arsenal of effective adjuvant composition(s) includes, for example, alum in combination with MPL, MPL in combination with TDM (O/W), and MPL in combination with TDM and CWS (O/W).

TABLE I

Similarities and differences between Vero/HSV vaccine and Skinner vaccine

| | Skinner Vaccine | Vero/HSV Vaccine |
|---|---|---|
| Cell substrate | MRC-5 | Vero |
| Infectious agent | HSV-1, Troisbell strain | HSV-2, g strain |
| Infection | High MOI (5) | Low MOI (0.1) |
| Serum deprivation of cells prior to/during infection | Yes | No |
| Duration of infection | 24 hours | 18 hours |
| Removal of FCS prior to cell harvesting | N/A | Yes |
| Detergent treatment | Nonidet NP40, 1%, 10 min @ RT | IGEPAL, 1%, 30 min on ice |
| Additional cell/virus lysis | No | Freeze-thaw (−80° C.) |
| Centrifugation | 650 g, 10 min | 4,000* g, 15 min |
| Removal of nuclei pellet | Yes | Yes |
| Occasional appearance of surface layer containing extra-particulate DNA (removed) | No | Yes |
| Centrifugation over sucrose gradient | Yes | No |
| Formaldehyde treatment of cytoplasmic fraction | Yes | No |
| Precipitation of proteins with aluminum hydroxide or acetone | Yes | No |
| Passage of lysates through columns with immobilized antibodies against cellular proteins | Yes | No |
| Filtering of lysate through molecular sieve (70 uM) | No | Yes |
| Dialysis | No | Yes |
| Residual virus in preparation | Present unless formaldehyde treatment is used | Below detectable even without formaldehyde** treatment (measured by plaque assay and by the more sensitive PCR method) |

*Higher centrifugation speed permits removal of not only nuclei contained in the pellet but also extra-particulate DNA (which occasionally appears as white stringy material in the Vero/HSV extracts at this stage).
**Formaldehyde treatment is avoided in Vero/HSV vaccine preparation because of the concern of modifying HSV antigens with a potential to subsequently induce aberrant immune response and lower-avidity antibodies to such antigens.

In a representative method of preparing the HSV antigen, the following steps were performed using routine laboratory techniques:

Vero cells were cultured in Eagle's Minimum Essential Medium (EMEM) supplemented with 10% FBS, 1% L-glutamine, gentamicin, and fungizone (that is, complete EMEM).

Subconfluent monolayers of Vero cells were washed twice in 175 cm² flasks with PBS and the cells were infected with 5×10⁵ PFU of HSV-2 (G) per flask diluted in EMEM alone.

After 1 hour of infection, virus solution was removed and cells were re-plated in flasks complete EMEM. The cells were cultured in a 37° C. $CO_2$ incubator for 18 hours.

After the 18-hour incubation, medium was removed and the cells were washed twice with 10 ml Tris-NaCl buffer (50 mM Tris, pH 7.5, 100 mM NaCl) with 2 mM EDTA.

5 ml of Tris-NaCl buffer with PMSF was added to the cells with 1% IGEPAL, and the flasks were placed on ice for 30 min (with agitation every 10 min) to begin to lyse the cells.

Cells were scraped from the flasks and collected into a pre-chilled 50 ml conical tube. An additional 1 ml of buffer was washed over the cell surface and added to the same collection tube.

The tube with cells was placed on dry ice and transferred to a −80° C. freezer for 3 hrs.

Lysis was completed by thawing the cells in the tube on wet ice and then briefly vortexing followed by centrifugation for 15 min at 4,000 g.

A white cloudy mass of DNA, which only occasionally appears at the top of the centrifuged tube, was removed with a pipette tip and discarded.

The remaining lysate was passed through a 70 μM sieve and subjected to centrifugation for 30 min at 4,000 g.

The supernatant was transferred to a new tube, dialyzed against 2 changes of PBS at 4° C. using SnakeSkin Pleated Dialysis Tubing (Pierce #68100, 10,000 MW cut-off).

The contents of the dialysis tube were transferred into a 50 ml tube, centrifuged for 30 min at 4,500 rpm at 4° C.

The resulting supernatant was transferred to a clean tube (without touching the pellet).

The supernatant containing the extract of detergent-treated, HSV-infected cells (that is, the vaccine antigen) was aliquoted and stored in a −80° C. freezer.

In an alternative method of preparing the HSV antigen, the cell extract was subjected to additional processing to further reduce DNA content.

In another alternative method of preparing the HSV antigen, the cell extract was subjected to additional processing to precipitate proteins from the extracts (for example, using aluminum hydroxide, acetone precipitation, or alternative methods well known in the art).

In another alternative method of preparing the HSV antigen, the cell extract was enriched in HSV proteins (for example, by passing the cell lysates through a column on which antibodies against HSV were immobilized with subsequent elution of bound material).

In another alternative method of preparing the HSV antigen, the cell extract was subjected to additional processing to reduce the presence of Vero proteins (for example, by passing the cell lysates through a column on which antibodies against Vero proteins are immobilized).

In another alternative method of preparing the HSV antigen, the cell extract was enriched in certain HSV proteins based on molecular weight and/or additional characteristics (for example, post-translational modifications known in the art such as glycosylation, and/or differences in hydrophobicity, hydrophilicity, charge, lipid association, etc.).

In other alternative methods of preparing the HSV vaccine compositions, the following were used to prepare 100 μl of vaccine composition (100 μl/100 g weight was effective in the cotton rat model but for human use it should initially be prorated based on the weight differences between the species as known and determined by routine experimentation by persons skilled in the art):

Vero/HSV+MPL+alum

Vero/HSV 50 ul; aluminum hydroxide 0.5-1% final concentration; MPL 25-50

Vero/HSV+MPL+TDM (O/W)

Vero/HSV 50 μl; MPL and TDM: 2.5 μg each in squalene oil, 0.2% Tween 80, water

Vero/HSV+MPL+TDM+CWS (O/W)

Vero/HSV 50 μl; MPL, TDM, CWS: 2.5 μg each in squalene oil, 0.2% Tween 80, water Possible variations in the Vero/HSV antigen may include, for example, the following: Vero cells infected with HSV-1; Vero cells infected with HSV-2 and HSV-1 simultaneously; and a mixture of extracts of HSV-2-infected Vero cells and HSV-1-infected Vero cells.

Each reference referred to within this disclosure is hereby incorporated in its respective entirety.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, because numerous modifications will readily occur to those skilled in the art, it is not desired to limit the invention to the exact construction and operation illustrated and described, and accordingly, all suitable modifications and equivalents may be resorted to, falling within the scope of the invention.

We claim:

1. A herpes simplex virus immunogenic composition, comprising:
   (a) an extract of detergent-treated and freeze-thawed herpes simplex virus-infected cells; and
   (b) an adjuvant,
   wherein said virus-infected cells are selected from the group consisting of Vero cells infected with herpes simplex virus-2, Vero cells infected with herpes simplex virus-1, and Vero cells infected with herpes simplex virus-2 and herpes simplex virus-1, and
   wherein said adjuvant is selected from the group consisting of: a combination of monophosphoryl lipid A (MPL) or a synthetic analogue thereof plus trehalose 6,6'-dimycolate (TDM) or a synthetic analogue thereof; and a combination of MLP or a synthetic analogue thereof plus TDM or a synthetic analogue thereof, plus biologically-active components of cell wall skeleton or synthetic analogues thereof.

2. A method of preparing the herpes simplex virus immunogenic composition of claim 1, comprising:
   (a) propagating Vero cells;
   (b) infecting said cells with herpes simplex virus-2, herpes simplex virus-1, or a combination of herpes simplex virus-2 and herpes simplex virus-1;
   (c) lysing the infected cells to obtain a cell extract by treatment with a detergent and at least one cycle of freezing and thawing;
   (d) purifying the cell extract; and
   (e) combining said cell extract with an adjuvant,
   wherein said adjuvant is selected from the group consisting of: a combination of monophosphoryl lipid A (MPL) or a synthetic analogue thereof plus trehalose 6,6'-dimycolate (TDM) or a synthetic analogue thereof, and a combination of MLP or a synthetic analogue thereof, plus TDM or a synthetic analogue thereof, plus biologically-active components of cell wall skeleton or synthetic analogues thereof, and wherein the combination of said adjuvant and the purified cell extract is said herpes simplex virus immunogenic composition.

3. The method of claim 2, wherein said detergent is octylphenoxy poly(ethyleneoxy)ethanol, branched.

4. The method of claim 2, wherein said purification is selected from the group consisting of removal of DNA, centrifugation, and/or dialysis.

5. The method of claim 2, wherein said purified cell extract is subjected to additional processing to precipitate proteins from said purified cell extract.

6. The method of claim 2, wherein said purified cell extract is subjected to additional processing to obtain herpes simplex virus-enriched proteins.

7. The method of claim 6, wherein said herpes simplex virus-enriched proteins are selected from the group consisting of high molecular weight proteins, low molecular weight proteins, glycosylated proteins, lipid-associated proteins, charged proteins, hydrophobic proteins, hydrophilic proteins, other post-translationally modified proteins, and combinations thereof.

8. The method of claim 2, wherein said purified cell extract is subjected to additional processing to reduce the presence of Vero cell native proteins.

9. A method of immunization of an animal or human against herpes simplex virus and herpes simplex virus-associated disease, comprising at least one administration of an effective amount of the herpes simplex virus immunogenic composition of claim 1.

10. The method of claim 9, wherein said herpes simplex virus immunogenic composition is administered intramuscularly, intravenously, intradermally, subcutaneously, or orally.

11. A herpes simplex virus immunogenic composition, comprising:

(a) an extract of detergent-treated herpes simplex virus-infected cells obtained by at least two sequential centrifugation steps; and (b) an adjuvant, wherein said virus-infected cells are selected from the group consisting of Vero cells infected with herpes simplex virus-2, Vero cells infected with herpes simplex virus-1, and Vero cells infected with herpes simplex virus-2 and herpes simplex virus-1, and wherein said adjuvant is selected from the group consisting of: a combination of monophosphoryl lipid A (MPL) or a synthetic analogue thereof plus trehalose 6,6'-dimycolate (TDM) or a synthetic analogue thereof; and a combination of MLP or a synthetic analogue thereof plus TDM or a synthetic analogue thereof, plus biologically-active components of cell wall skeleton or synthetic analogues thereof.

12. A method of preparing the herpes simplex virus immunogenic composition of claim 11, comprising:

(a) propagating Vero cells;

(b) infecting said cells with herpes simplex virus-2, herpes simplex virus-1, or a combination of herpes simplex virus-2 and herpes simplex virus-1;

(c) lysing the infected cells to obtain a cell extract by treatment with a detergent and at least one cycle of freezing and thawing;

(d) purifying the cell extract; and (e) combining said cell extract with an adjuvant, wherein said adjuvant is selected from the group consisting of: a combination of monophosphoryl lipid A (MPL) or a synthetic analogue thereof plus trehalose 6,6'-dimycolate (TDM) or a synthetic analogue thereof, and a combination of MLP or a synthetic analogue thereof, plus TDM or a synthetic analogue thereof, plus biologically-active components of cell wall skeleton or synthetic analogues thereof, and wherein the combination of said adjuvant and the purified cell extract is said herpes simplex virus immunogenic composition.

13. The method of claim 12, wherein said detergent is octylphenoxy poly(ethyleneoxy)ethanol, branched.

14. The method of claim 12, wherein said purification is selected from the group consisting of removal of DNA, centrifugation, and/or dialysis.

15. The method of claim 12, wherein said purified cell extract is subjected to additional processing to precipitate proteins from said purified cell extract.

16. The method of claim 12, wherein said purified cell extract is subjected to additional processing to obtain herpes simplex virus-enriched proteins.

17. The method of claim 16, wherein said herpes simplex virus-enriched proteins are selected from the group consisting of high molecular weight proteins, low molecular weight proteins, glycosylated proteins, lipid-associated proteins, charged proteins, hydrophobic proteins, hydrophilic proteins, other post-translationally modified proteins, and combinations thereof.

18. The method of claim 12, wherein said purified cell extract is subjected to additional processing to reduce the presence of Vero cell native proteins.

19. A method of immunization of an animal or human against herpes simplex virus and herpes simplex virus-associated disease, comprising at least one administration of an effective amount of the herpes simplex virus immunogenic composition of claim 11.

20. The method of claim 19, wherein said herpes simplex virus immunogenic composition is administered intramuscularly, intravenously, intradermally, subcutaneously, or orally.

* * * * *